(12) United States Patent
Artal Soriano et al.

(10) Patent No.: US 9,572,490 B2
(45) Date of Patent: Feb. 21, 2017

(54) METHOD AND SYSTEM FOR MEASURING INTRAOCULAR SCATTERING

(75) Inventors: Pablo Artal Soriano, Murcia (ES); Guillermo Perez Sanchez, Murcia (ES); Juan Manuel Bueno Garcia, Murcia (ES); Harilaos Ginis, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 420 days.

(21) Appl. No.: 14/114,354

(22) PCT Filed: Apr. 11, 2012

(86) PCT No.: PCT/ES2012/070242
§ 371 (c)(1),
(2), (4) Date: Apr. 1, 2014

(87) PCT Pub. No.: WO2012/146813
PCT Pub. Date: Nov. 1, 2012

(65) Prior Publication Data
US 2014/0211154 A1    Jul. 31, 2014

(30) Foreign Application Priority Data

Apr. 28, 2011  (ES) .................................. 201130670

(51) Int. Cl.
| | |
|---|---|
| *A61B 3/14* | (2006.01) |
| *A61B 3/00* | (2006.01) |
| *A61B 3/10* | (2006.01) |
| *A61B 3/12* | (2006.01) |
| *A61B 3/103* | (2006.01) |

(52) U.S. Cl.
CPC . *A61B 3/12* (2013.01); *A61B 3/10* (2013.01); *A61B 3/103* (2013.01)

(58) Field of Classification Search
CPC ........... A61B 3/14; A61B 3/103; A61B 3/113; A61B 3/1208; A61B 3/1225; A61B 3/024; A61B 3/032; A61B 3/18; A61B 3/1015
USPC ................ 351/206, 200, 205, 210–211, 218, 351/221–223, 245–246
See application file for complete search history.

(56) References Cited

U.S. PATENT DOCUMENTS

2002/0097376 A1    7/2002  Applegate et al.

FOREIGN PATENT DOCUMENTS

| EP | 2147633 A1 | 1/2010 |
|---|---|---|
| WO | 2005122785 A1 | 12/2005 |

OTHER PUBLICATIONS

International Search Report from international application No. PCT/ES2012/070242, with an international filing date of Apr. 11, 2012, mailed from the Spanish Patent and Trademark Office on Aug. 7, 2012.

(Continued)

*Primary Examiner* — Dawayne A Pinkney
(74) *Attorney, Agent, or Firm* — Baker & Hostetler LLP

(57) ABSTRACT

The present invention relates to a method for measuring ocular scattering, comprising the steps of: sequentially projecting images from an extensive light source, corresponding to different visual angles, onto the retina; recording the output light in a camera or detector once it has passed through the eye twice; calculating the intensity at the center of each recorded image; calculating the PSF for each angle from the previous intensities; and calculating the average of the value of the PSF between the angles. The invention also relates to a system for carrying out said method. The invention can be used to measure the intensity of the scattered light in an objective manner.

12 Claims, 6 Drawing Sheets

(56) References Cited

OTHER PUBLICATIONS

Diaz-Douton, et al., Comparison of the Retinal Image Quality with a Hartmann-Shack Wavefront Sensor and a Double-Pass Instrument, Investigative Opthalmology & Visual Science, Apr. 2006, pp. 1710-1716, vol. 47., No. 4, Association for Research in Vision and Opthalmology, Rockville, MD, US.

Santamaria, et al., Determination of the point-spread function of human eyes using a hybrid optical-digital method, Journal of the Optical Society of America, Jun. 1987, pp. 1109-1114, vol. 4, No. 6, Optical Society of America, Washington, D.C., US.

METHOD AND SYSTEM FOR MEASURING INTRAOCULAR SCATTERING

CROSS-REFERENCE TO RELATED APPLICATIONS

The present application claims the benefit of Spanish application serial no. P201130670, with a filing date of Apr. 28, 2011, and claims the benefit of International application serial no. PCT/ES2012/070242 titled METHOD AND SYSTEM FOR MEASURING INTRAOCULAR SCATTERING with a filing date of Apr. 11, 2012.

FIELD OF THE INVENTION

The present invention is comprised in the field of ophthalmic systems, visual optics and ophthalmology.

The invention particularly relates to an optical system and a method for the non-invasive and objective determination of intraocular scattering in the human eye by means of recording and analyzing images projected onto the retina.

BACKGROUND OF THE INVENTION

The objective examination of intraocular scattering, which occurs when light interacts with ocular structures before forming the image on the retina, is particularly important for improving the early diagnosis of some of the most widespread ocular pathologies, particularly cataracts, which is the pathology that causes the highest rate of blindness worldwide, but also dry eye syndrome, corneal edema, etc.

Optical quality of the retinal image is the first determining factor of visual capacity. Like any optical system, the study of the eye in terms of its optical quality is approached by means of analyzing geometric characteristics, such as the shape of the cornea and the lens or the axial length, and also by analyzing the intrinsic properties of the ocular media with which light interacts on its way to the inner portion of the eye. In relation to the geometric characteristics of ocular surfaces, wavefront sensors (Prieto et al., 2000) evaluate aberrations of the eye, and therefore optical quality of the eye can be represented through PSF (Point Spread Function). The form of this function is determined by the geometric quality of ocular surfaces, the refractive index gradient and the axial length of the eye. The difference between an ocular PSF and the theoretical form of the function, which is obtained by assuming that the eye is a perfect optical system limited only by diffraction, relates to the induction of aberrations of the eye. However, although the intraocular scattering produced by the non-uniformity of the ocular media also heavily determines the quality of the retinal image, the characterization thereof is not included in the description of optical quality in terms of aberrations of the eye (Díaz-Doutón, Benito, Pujol, Arjona, Güell, & Artal, 2006). Intraocular scattering originates from the interaction of light with non-uniformities in the refractive index distribution of the ocular media, and it causes the light to scatter on the fundus of the eye, instead of directing the focused light to the central retina. The extension of this light scattering is described using statistical terms. Intraocular scattering can have a serious impact on vision, especially when natural scenes with the presence of bright sources are observed. An example is standard night driving conditions. Scattered light inside the eye causes retinal image contrast to decrease, and this therefore results in a serious reduction of vision quality.

Though treated separately due to the different causes producing them, aberrations of the eye and intraocular scattering both affect retinal image quality. The double-pass technique (Santamaria, Artal, & Bescos, 1987) based on projecting a collimated beam onto the patient's retina and directly recording the light reflected back allows characterizing the effect of aberrations of the eye and intraocular scattering on the point source projected onto the retina. Information on intraocular scattering is, however, restricted to analyzing the recorded retinal area, which is generally less than 1% the field of view. In current clinical use of the double-pass instrument (US 2010/0195876, 2008; Artal et al., PLOS One, 2011), information relating to intraocular scattering is estimated by means of analyzing the intensity recorded in the periphery of the double-pass image with respect to the total intensity of the PSF. The limitation of this technique lies in the fact that since the intensity of PSF drops rapidly with the angle from the central maximum to the most eccentric areas, only the smallest angles can be evaluated. Beyond a half degree of eccentricity, the intensity of the light in the PSF of a normal eye is so low that it is impossible to discriminate the signal from the background, and therefore only scattering at small angles can be evaluated. Furthermore, most clinical instruments used today use infrared light to generate the point source on the retina, the image of which is subsequently analyzed to estimate the intraocular scattering produced. Although this characteristic is suitable for minimizing the discomforts of a visible light beam visible for the subject, it is not optimal for obtaining a good estimate of intraocular scattering. The interaction of infrared light with the fundus of the eye produces a high level of scattered light, and although this does not affect visual capacity, it does contribute to estimating light scattered onto the double-pass image. Considering these limitations, the standard technique for analyzing double-pass images to estimate intraocular scattering is restricted to analyzing a limited region around peak or central maximum of the recorded image. This limitation in turn means that the presence of aberrations of the eye, modifying the distribution of intensity on the double-pass image also in this zone closest to the peak, could lead to interpreting an increase in the intensity around the peak that was actually produced by the effect of aberrations of the eye as scattered light. Although the effect of low order aberrations, such as defocusing, can be minimized to restrict the analysis of double-pass images, the contribution of high order aberrations cannot be completely eliminated in a clinical setting. Therefore, the estimate of intraocular scattering based on the double-pass technique with a point source seems particularly suitable for those cases in which the amount of scattered light is relatively high, like in a cataract process or in severe dry eye syndromes, but it does not seem suitable for general use as a technique for estimating the level of scattered light in normal eyes or in eyes with incipient pathologies occurring with a progressive increase in intraocular scattering.

Similar limitations are also shared by methods designed to characterize intraocular scattering from analyzing images recorded with a Hartmann-Shack sensor (Thibos & Hong, 1999). The dynamic range of the images analyzed in this case is also too low to enable discriminating scattered light above the fundus level intrinsic to the measurement. Other objective techniques for estimating intraocular scattering have been proposed, such as measuring dynamic scattering (Datiles, Ansari, & Reed, 2002; Vivino, Chintalagiri, Trus, & Datiles, 1993), but none of these techniques is suitable for being used in clinical environments; in fact, up until now none of these techniques had been implemented in a clinical instrument.

On the other hand, there are other systems that seek to estimate the magnitude of scattered light in the eye from psychophysical, and therefore subjective, measurements. Some examples are the visual acuity test designed by Holladay (Holladay, Prager, Trujillo, & Ruiz, 1987), which evaluates the drop in visual acuity produced by the presence of glaring sources in the field of view. The patient looks at the acuity test through a hole in a hemisphere. Illumination of the inner face of this hemisphere can be externally controlled by the operator such that changes in visual acuity of the subject caused by increasing levels of intensity in the light inside the hemisphere can be measured. Other subjective methods are also based on examining the effect of glaring sources on different visual functions such as contrast sensitivity (Bailey & Bullimore, 1991). Another psychophysical method is the direct compensation method based on the presentation of a glaring ring-shaped source with oscillating intensity and the compensation of this effect in the fovea through the control of a central source the intensity of which oscillates in counterphase to the glaring ring-shaped source. This method was implemented in the stray-light meter (van den Berg & IJspeert, 1992). An improved version of this methodology, the compensation comparison method (Franssen, Coppens, & van den Berg, 2006), was subsequently proposed. This device has been used in different applications related to estimating intraocular scattering (van den Berg, et al. 2007). The fundamental limitation of this instrument is the same as with other subjective systems because it requires the active participation of the subject in the measurement process. In this device, the participation requirement is especially demanding because the compensation comparison method entails getting the subject involved in a sequence of forced decisions related to the relative luminance of two rapidly changing central semifields. This process of forced, consecutive and rapid decisions obviously involves problems for many subjects, particularly for those in whom the reliable estimate of intraocular scattering is particularly relevant, as in elderly subjects.

Until now, there has not been any optical instrument capable of suitably measuring the intensity of scattered light in normal (non-pathological) eyes from a purely optical measurement, i.e., from an objective technique and without requiring active intervention of the subject. Therefore, there is a need for an optical instrument capable of carrying out a method for objectively measuring intraocular scattering at large field of view angles, for example up to 10°. Furthermore, it is especially relevant that this system allows measuring using different wavelengths, because the dependence of scattered light with incident wavelength is strongly related to the typology of the non-uniformities created by the scattering. Therefore, being able to access this characterization with the wavelength may provide relevant information concerning the underlying pathology.

OBJECT OF THE INVENTION

The object of the invention is to palliate the technical problems discussed in the preceding section. To that end, the invention proposes a double-pass configuration for recording the distribution of intensity on the retina propagated through the optics of the eye. As previously described, the term double-pass refers to the fact that the retinal image is recorded once the light has passed through the optics of the eye twice, once in its inlet path and again in its outlet path from the retina. A fundamental difference between the invention described herein and the double-pass instruments used until now lies in the fact that estimating scattered light is performed on images of extensive objects projected onto the retina, instead of point sources. The method comprises the steps of: sequentially projecting images from an extensive light source, corresponding to different eccentricities in the retina, onto the retina (subtending different visual angles); recording the output light once it has passed through the eye twice; calculating the intensity at the center of each recorded image; calculating the PSF for each angle from the previous intensities; and calculating the average of the value of the PSF between the angles. The visual angles preferably range from 0.01 to 10 degrees. The extensive object is preferably a ring or circle (ring having radius 0). Diaphragms can be used in the illumination arm and in the recording arm, such that a first diaphragm is conjugated with the pupil before the image is projected onto the retina and a second diaphragm is conjugated with the pupil plane before the image is recorded to control the portion of the pupil area through which the output light of the eye is recorded. The dimension of the projected image can be controlled by means of an aperture. Spectral analysis of the recorded signal can be performed if a source having a broad spectral range is used. In this case the wavelength is preferably between 400 nm and 700 nm and bandwidth between 5 nm and 50 nm, and it can be selected with a spectral filter. The system of the invention is a double-pass optoelectronic system that includes programming means for carrying out the calculations, an optical system with lenses and diaphragms, means for recording the image (detector, camera . . . ) and an extensive light source, which can be a liquid crystal modulator illuminated by a halogen lamp having a broad spectral range or a translucent film backlit by LEDs. It can further incorporate means for correct alignment of the eye with the optical system and means for synchronizing the source and the detector or camera to prevent unnecessary exposures of the retina.

The method of the invention allows characterizing the level of scattered light at eccentricity levels of 20° on the field of view, which is an inaccessible range with current methods, in addition to providing more complete measurements in eyes with a high level of scattering, and it can be used in non-pathological eyes.

BRIEF DESCRIPTION OF THE DRAWINGS

For the purpose of aiding to better understand the features of the invention according to a preferred practical embodiment thereof, the following description of a set of drawings is attached where the following has been depicted with an illustrative character:

FIG. 5a shows two semicircular apertures, whereas FIG. 5b shows a circular sub-aperture and a concentric ring.

DETAILED DESCRIPTION OF THE INVENTION

Figure 1A:
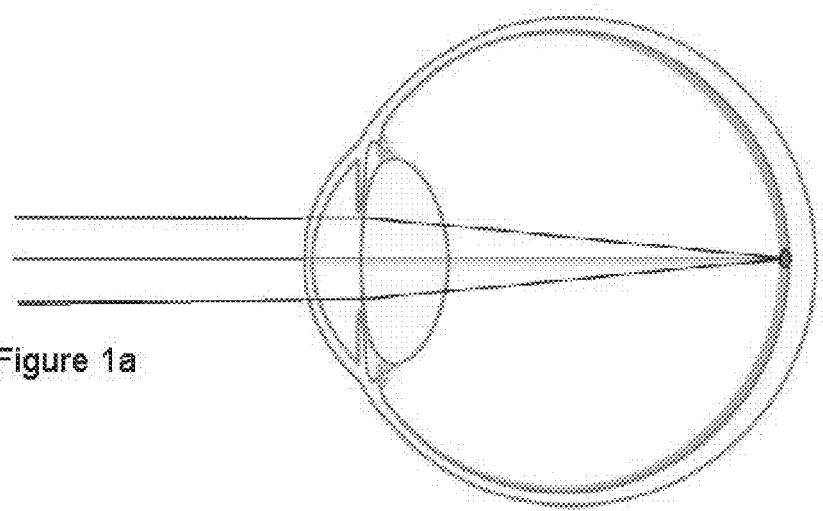
FIG. 1 shows the diagram of an eye forming the image of a far point source, focusing on a small proportion of the retina (FIG. 1a) and the result when the light of this beam interacts with non-uniformities of the ocular media and is partially scattered onto the fundus of the eye (FIG. 1b).
Figure 1B:
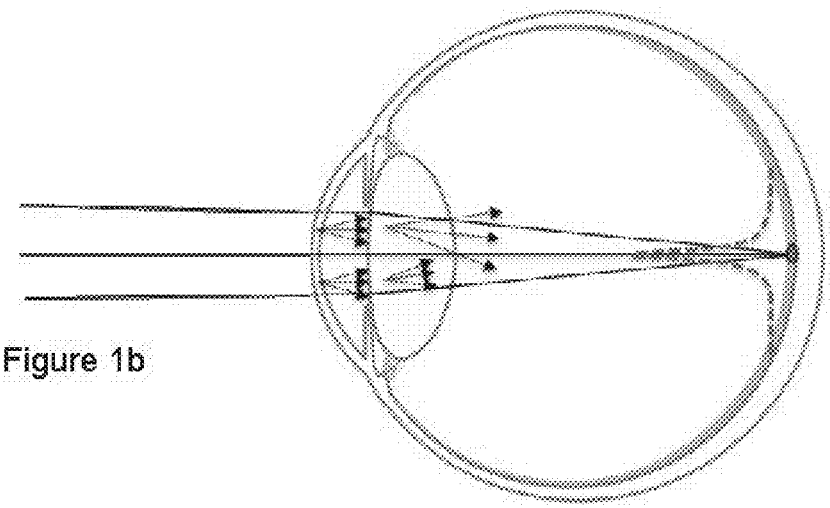
Figure 2A:
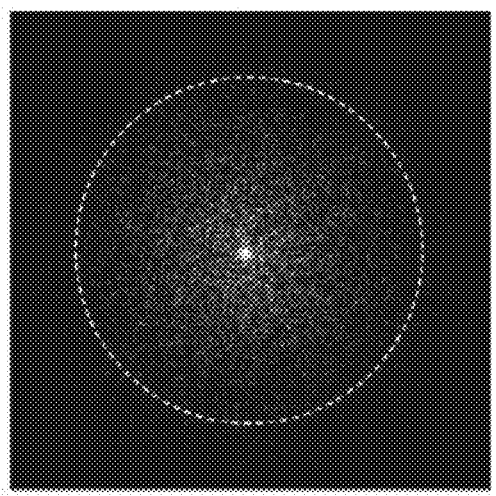
FIG. 2 shows the PSF of an eye with intraocular scattering (FIG. 2a) and the image of an extensive object (uniformly illuminated disc) through this system (FIG. 2b).
Figure 2B:
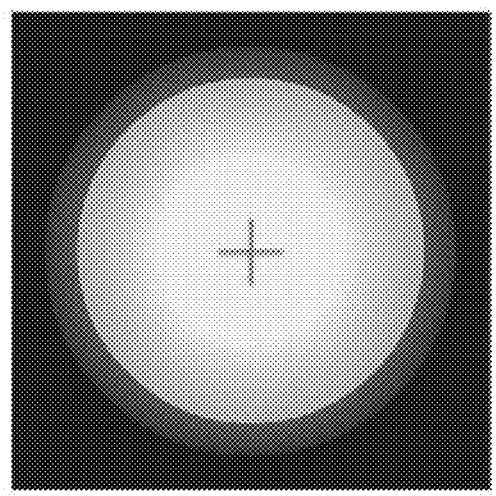

FIG. 2a shows the PSF of an eye with intraocular scattering. FIG. 2b shows the image of a uniformly illuminated disc, such as a particular case of a ring with inner radius 0, through this system. It is verified that if the ratio of energy in a circle having radius R with respect to the total energy of the PSF is $I_c$ (where $0<I_c<1$), therefore the fraction of the intensity at the center of a disc having radius R with respect to the intensity of an infinite disc is also equal to $I_c$. This ratio is equal to:

$$I_c = \int_0^\theta 2\pi\varphi \cdot PSF(\varphi)d\varphi \qquad \text{(Equation 1)}$$

where $PSF(\varphi)$ is the PSF of the system (including scattering) and $\theta$ is the radius of the circle in FIG. 2a, or of the disc in FIG. 2b. In both cases, it is assumed that the PSF is normalized $$\left(\int_0^{\pi/2} 2\pi\varphi \cdot PSF(\varphi)d\varphi = 1\right),$$

i.e., the central intensity of a complete disc is equal to 1.

Figure 3:
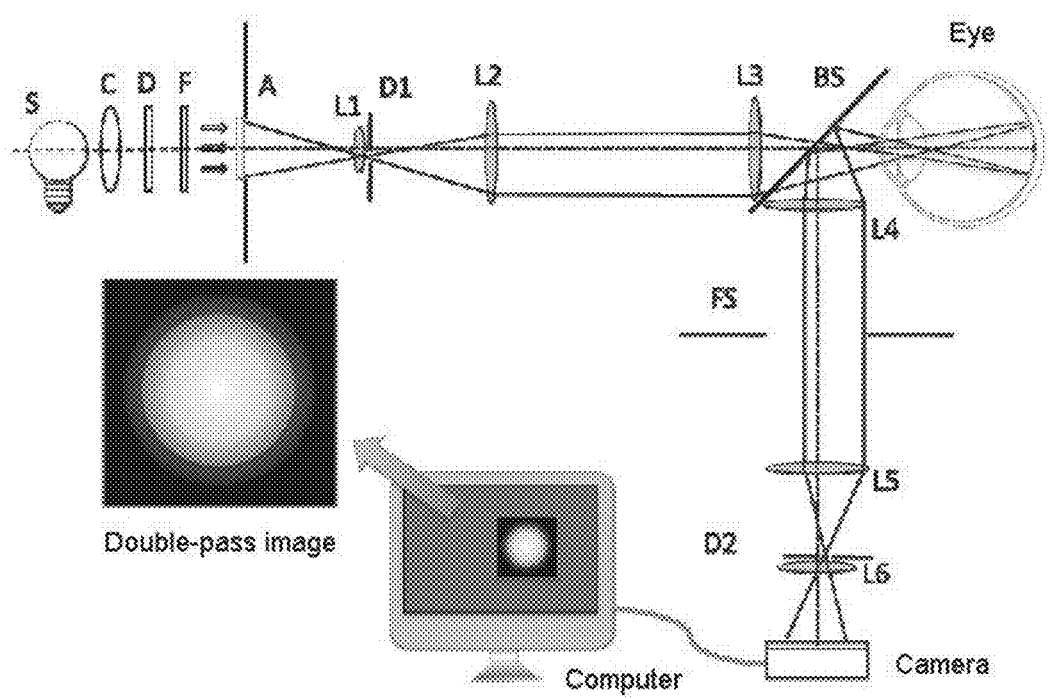
FIG. 3 shows a possible version of the proposed double-pass system where an extensive object is projected onto the retina.

FIG. 3 shows a possible implementation of the double-pass system of the invention, in which images are projected sequentially, subtending different visual angles corresponding to different eccentricities of the retina. The extensive object would be a ring having inner radius $R_0$ and outer radius R illuminated by a source S, or a circle like in the example, which is not more than a ring with inner radius $R_0=0$. The light projected by this object can be collimated by the optic C to subsequently be propagated through the scatterer D and filters F. The dimension of the disc can be controlled by the aperture A. The image of this extensive object is projected onto the retina of the eye using lenses L1, L2 and L3. The diaphragm D1 is conjugated with the pupil of the eye (by means of lenses L2 and L3) to enable thus controlling the portion of the pupil through which the object is projected towards the fundus of the eye.

The image of the circle projected onto the retina can then be recorded using a beam splitter (BS) and lenses L4, L5 and L6. The diaphragm D2 is conjugated with the pupil plane (by means of lenses L4 and L5) to enable thus controlling the portion of the pupil area through which the output light of the eye is recorded. Diaphragms D1 and D2 can be arranged such that the projection of the object and the recording are done in different zones of the pupil area, such that light reflected on ocular surfaces is prevented from contributing to the intensity of the image recorded on the camera or the detector. Estimating scattered light is thus not affected by the contribution of back-scatter, "backwardly" scattered light, in the inlet path of the light in the eye, which enables restricting the analysis to forward-scatter, or "forwardly" scattered light, which is the scattered light component directly related to visual quality loss (de Waard, et al. 1992).

Figure 4:
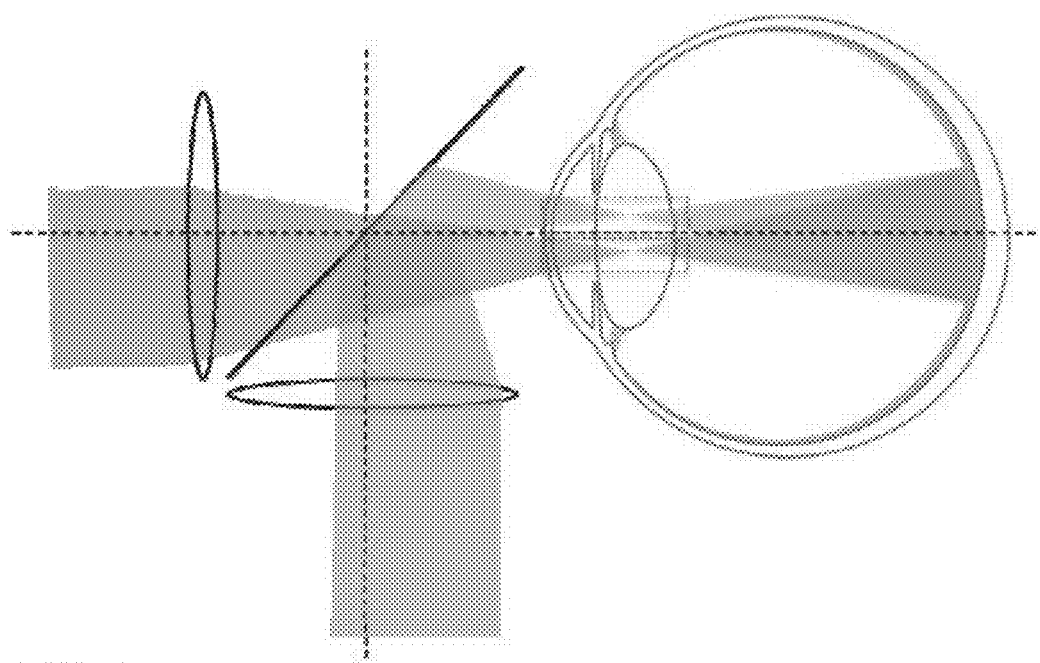
FIG. 4 shows how the illumination and the recording can be done through different portions of the pupil of the eye.

FIG. 4 shows how the illumination and the recording can be done through different portions of the pupil of the eye. The diaphragms do not necessarily have to be circular: the same effect can be achieved with other shapes, such as a ring-shaped mask at the inlet and a central circular shape at the outlet, provided that the diaphragms are different and do not overlap when projected onto the pupil.

Figure 5:
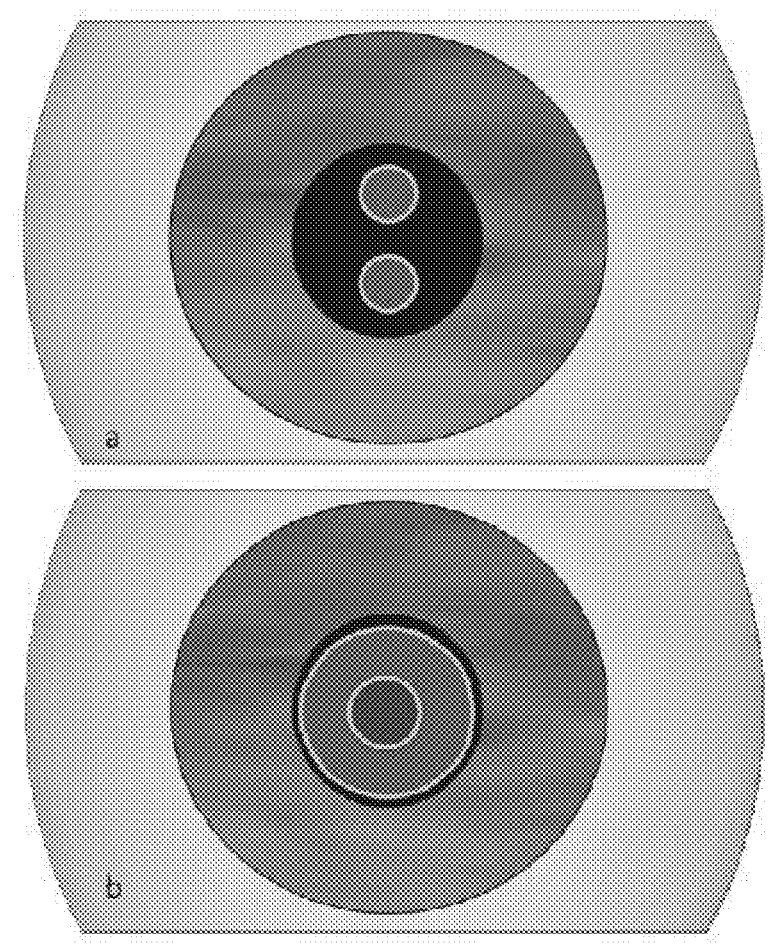
FIG. 5 shows two different methods for separating the pupil area into two different portions for the illumination and the recording of the object projected onto the retina.

FIG. 5 shows two different methods for separating the pupil area into two different portions for the illumination and the recording of the object projected onto the retina. FIG. 5a shows two semicircular apertures, whereas FIG. 5b shows a circular sub-aperture and a concentric ring.

In reference to the embodiment of FIG. 3, the extensive object can be generated by a liquid crystal modulator illuminated by a halogen lamp having a broad spectral range, and where the light generated by the source is collimated and homogenized by means of the collimator C and the scatterers D. The spectral filter F allows selecting the spectral profile of the light that will strike the eye. The selected wavelength is preferably 400 nm to 700 nm, with a bandwidth of 5 to 50 nm. The use of a source having a broad spectral range, combined with the use of filters or other elements capable of selecting a specific section of the spectral range, allows estimating intraocular scattering with different wavelengths of the incident light (from red to blue). This characteristic is especially relevant for diagnosing potential pathologies responsible for a specific level of intraocular scattering because analysis of the relationship between the scattered light profile and the incident wavelength allows establishing hypotheses as to the type of scattering centers responsible for intraocular scattering in each case (Coppens, et al. 2005).

The dimensions of the disc are controlled by means of a computerized spatial modulator. An image of the object is projected onto the retina of the eye through lenses L1, L2 and L3. The diaphragm D1 is conjugated with the pupil of the eye (by means of lenses L2 and L3) to enable thus controlling the portion of the pupil through which the object is projected towards the fundus of the eye. The image of the disc projected onto the retina can then be recorded using a beam splitter (BS) and lenses L4, L5 and L6. The diaphragm D2 is conjugated with the pupil plane (by means of lenses L4 and L5) to enable thus controlling the portion of the pupil area through which the output light of the eye is recorded. The diaphragms D1 and D2 can be arranged such that the projection of the object and the recording are done in different zones of the pupil area, such that light reflected on ocular surfaces is prevented from contributing to the intensity of the image recorded on the camera or the detector.

A series of discs corresponding to visual angles ranging from 0.01 to 10 degrees are projected onto the retina sequentially. The intensity at the center of each disc is recorded. The derivative of this intensity with respect to the radius of the disc is numerically estimated by the finite difference method. The derivative divided by $2\pi$ times the angle of each disc is equal to the PSF of the double-pass at the corresponding angle. This can be explained by taking the derivative of Equation 1 (where the PSF is the autocorrelation of the PSF of the system, characteristic of the double-pass), resulting in Equation 2:

$$PSF(\vartheta) = \frac{1}{2\pi\vartheta} \frac{dI_c(\vartheta)}{d\vartheta} \quad \text{(Equation 2)}$$

Equation 1 can be approached using finite differences according to:

$$PSF(\vartheta_n) = \frac{1}{2\pi\vartheta_n} \frac{I_c(\vartheta_{i+1}) - I_c(\vartheta_i)}{\vartheta_{i+1} - \vartheta_i} \quad \text{(Equation 3)}$$

where $\vartheta_i$ is the radius of consecutive discs and $\vartheta_n = (\vartheta_{i+1} + \vartheta_i)/2$.

The average of the value of the PSF between angles from 0.5 to around 10° is a magnitude that characterizes intraocular scattering (CIE 135-1999).

If necessary, the PSF corresponding to the single-pass through the ocular media can be numerically calculated from that corresponding to the double-pass and using Fourier treatment-based deconvolution techniques.

Figure 6:
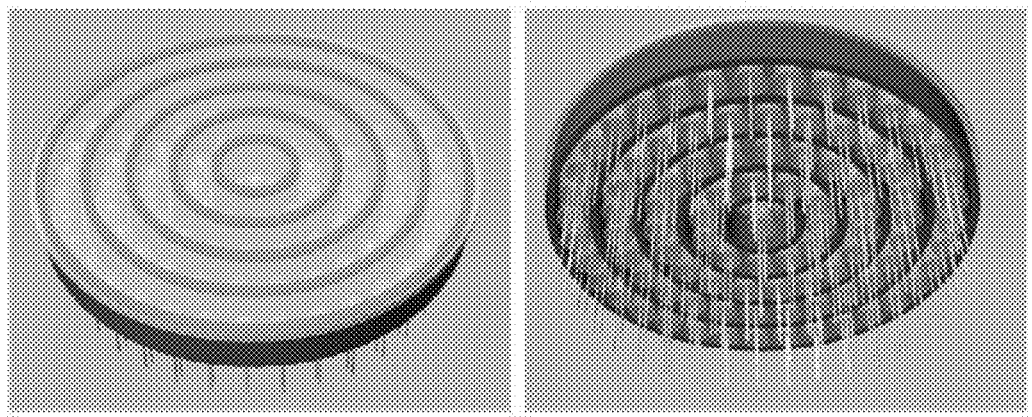
FIG. 6 shows an example of an extensive object incorporated in the invention which can be generated with a translucent material backlit by independent, LED-type sources.

In another embodiment, the extensive object is a translucent film backlit by LEDs as shown in FIG. 6. The intensity of the light can be homogenized by scatterers D and suitable spacing between diodes. The dimension of the generated disc can be controlled by means of the number of diodes concentrically illuminated. An image of the object is projected onto the retina of the eye through lenses L1, L2 and L3. The diaphragm D1 is conjugated with the pupil of the eye (by means of lenses L2 and L3) to enable thus controlling the portion of the pupil through which the object is projected towards the fundus of the eye. The image of the disc projected onto the retina can be recorded by means such as a CCD camera or a photodetector using a beam splitter (BS) and lenses L4, L5 and L6. The diaphragm D2 is conjugated with the pupil plane (by means of lenses L4 and L5) to enable thus controlling the portion of the pupil area through which the output light of the eye is recorded. The diaphragms D1 and D2 can be arranged such that the projection of the object and the recording are done in different zones of the pupil area, such that light reflected on ocular surfaces is prevented from contributing to the intensity of the image recorded on the camera or the detector.

By illuminating different concentric distributions of LEDS in a controlled manner, a series of discs corresponding to visual angles preferably ranging from 0.01 to 10 degrees are projected onto the retina. The intensity at the center of the recorded image of each disc is recorded in the camera or the detector. Each concentric disc of LEDs is modulated at a specific frequency to be able to discriminate its effect in the subsequent analysis of frequencies. The isolated contribution of each ring on the central area recorded is extracted by means of the spectral analysis of the recorded signal.

The device of the invention preferably has means for assuring correct alignment of the eye with respect to the optics of the system and means for synchronizing the source and the detector or camera to prevent unnecessary exposures of the retina.

LITERATURE

P. M. Prieto, F. Vargas-Martin, S. Goelz, P. Artal, J. Opt. Soc. Am. A, 17, 1388-1398 (2000). "Analysis of the performance of the Hartmann-Shack sensor in the human eye".

J. F. Díaz-Doutón, A. Benito, J. Pujol, M. Arjona, J. L. Guell, P. Artal, Invest. Ophthalmol. Vis. Sci., 47, 1710-1716 (2006). "Comparison of the retinal image quality with a hartmann-shack wavefront sensor and a double-pass instrument".

J. Santamaria, P. Artal, and J. Bescós, "Determination of the point-spread function of human eyes using a hybrid optical-digital method," J. Opt. Soc. Am. A 4, 1109-1114 (1987).

P. Artal, A. Benito, G. M. Pérez, E. Alcón, A. De Casas, J. Pujol, J. M. Marin, "An Objective Scatter Index Based on Double-Pass Retinal Images of a Point Source to Classify Cataracts", PLoS ONE, 6(2) (2011).

L N Thibos and X. Hong, "Clinical applications of the Shack-Hartmann aberrometer," Optom. Vision Sci. 76, 817-825 (1999).

Datiles M B, Ansari R R, Reed G F. (2002) A clinical study of the human lens with a dynamic light scattering device. Exp Eye Res 74:93 9.

Vivino M A, Chintalagiri S, Trus B, Datiles M (1993) Development of a Scheimpflug slit lamp camera system for quantitative densitometric analysis. Eye 7: 791-798.

Holladay J T, Prager T C, Trujillo J, Ruiz R S (1987) Brightness acuity test and outdoor visual acuity in cataract patients. J Cataract Refract Surg 13: 67-69.

J. Bailey, M A Bullimore (1991) A new test for the evaluation of disability glare. Optometry and Vision Science 68, 911-917.

Van den Berg T J, IJspeert, J K (1992) Clinical Assessment of Intraocular Stray Light. App. Opt. 31: 3694-3696.

Franssen L, Coppens J E, van den Berg T J (2006) Compensation comparison method for assessment of retinal straylight. Invest. Ophthalmol. Vis. Sci. 47: 768-776.

Van den Berg T J, van Rijn L J, Michael R, Heine C, Coeckelbergh T, et al., (2007). Straylight effects with aging and lens extraction. Am. J. Ophthalmol. 144: 358-363.

De Waard P W, IJspeert J K, van den Berg T J, de Jong P T, (1992), Intraocular light scattering in age-related cataracts. Invest. Ophthalmol. Vis. Sci. 33: 618-625.

What is claimed is:

1. A method for measuring ocular scattering comprising the steps of:
    sequentially projecting images of an extensive object from an extensive light source onto the retina of an eye, subtending different visual angles corresponding to different eccentricities of the retina;
    recording the output light in a camera or photodetector once it has passed through the eye twice;
        wherein a first diaphragm is conjugated with the pupil of the eye before the image is projected on the retina and a second diaphragm is conjugated with a pupil plane before the image is recorded to control the portion of the pupil area through which the output light of the eye is recorded;
    executing on a computer a computer program stored on a non-transitory computer readable medium encoded with instructions to perform the steps of:
        calculating the intensity at the center of each recorded image;
        reconstructing the broad-field Point Spread Function ("PSF") for each angle from the previously calculated intensities;
        calculating the average of the value of the PSF between the angles; and storing the average of the value of the PSF between the angles in a computer readable medium for use in diagnosing ocular pathology.

2. The method according to claim 1, where the subtended visual angles range from 0.01 to 10 degrees.

3. The method according to claim 1, wherein the extensive object is a ring having inner radius $R_0$ and outer radius R.

4. The method according to claim 1, wherein the extensive object is a circle or ring having inner radius $R_o=0$.

5. The method according to claim 1, further comprising controlling the dimension of the projected image by an aperture (A) means.

6. The method according to claim 1, wherein the step of sequentially projecting images is performed with an extensive light source having a broad spectral range.

7. The method according to claim 6, further comprising selecting with a spectral filter and the extensive light source, a wavelength between 400 nm and 700 nm and a bandwidth between 5 nm and 50 nm.

8. The method according to claim 6, further comprising, performing spectral analysis of the recorded signal of the output light.

9. A double-pass optoelectronic system comprising:
an extensive light source;
a display device;
at least one of a camera or photodetector;
a computer; and
a computer program stored on a non-transitory computer readable medium encoded with instructions executable by the computer to perform the steps of:
  transmitting to the extensive light source to sequentially project images of an extensive object from the extensive light source onto the retina of an eye, subtending different visual angles corresponding to different eccentricities of the retina;
  transmitting to at least one of a camera or photodetector to record the output light once it has passed through the eye twice;
    wherein a first diaphragm is conjugated with the pupil of the eye before the image is projected on the retina and a second diaphragm is conjugated with a pupil plane before the image is recorded to control the portion of the pupil area through which the output light of the eye is recorded;
  calculating the intensity at the center of each recorded image;
  reconstructing the broad-field Point Spread Function ("PSF") for each angle from the previously calculated intensities;
  calculating the average of the value of the PSF between the angles; and
  storing the average of the value of the PSF between the angles in a computer readable medium for use in diagnosing ocular pathology.

10. The double-pass optoelectronic system of claim 9, wherein the extensive light source comprises a translucent film backlit by LEDs.

11. The double-pass optoelectronic system according to claim 9, further comprising means for a correct alignment of the eye with the system and means for synchronizing the source and the detector or camera to prevent unnecessary exposures of the retina.

12. The double-pass optoelectronic system of claim 9, wherein the extensive light source comprises a liquid crystal modulator illuminated by a halogen lamp having a broad spectral range.

* * * * *